US010632278B2

(12) United States Patent
Kirszenblat et al.

(10) Patent No.: US 10,632,278 B2
(45) Date of Patent: Apr. 28, 2020

(54) EARPHONES FOR MEASURING AND ENTRAINING RESPIRATION

(71) Applicant: Bose Corporation, Framingham, MA (US)

(72) Inventors: Romain Kirszenblat, Allston, MA (US); Lifun Lin, Lincoln, MA (US); Mikhail Ioffe, Newton, MA (US); Tegan Ayers, Rochester, MA (US); Randy Michael Carbo, Hopedale, MA (US)

(73) Assignee: Bose Corporation, Framingham, MA (US)

( * ) Notice: Subject to any disclaimer, the term of this patent is extended or adjusted under 35 U.S.C. 154(b) by 262 days.

(21) Appl. No.: 15/655,853

(22) Filed: Jul. 20, 2017

(65) Prior Publication Data

US 2019/0022349 A1    Jan. 24, 2019

(51) Int. Cl.
*A61M 21/02* (2006.01)
*H04R 1/10* (2006.01)
(Continued)

(52) U.S. Cl.
CPC .......... *A61M 21/02* (2013.01); *A61B 5/6803* (2013.01); *A61B 5/6817* (2013.01);
(Continued)

(58) Field of Classification Search
CPC ...... A61M 2205/50; A61M 2021/0088; A61M 2021/0083; A61M 2021/0061;
(Continued)

(56) References Cited

U.S. PATENT DOCUMENTS

| 5,143,078 A | 9/1992 | Mather et al. |
| 7,850,619 B2 | 12/2010 | Gavish et al. |

(Continued)

FOREIGN PATENT DOCUMENTS

| GB | 2532745 A | 6/2016 |
| WO | 2010054863 A1 | 5/2010 |

(Continued)

OTHER PUBLICATIONS

International Search Report and Written Opinion dated Oct. 10, 2018 for International application No. PCT/US2018/043058.

(Continued)

*Primary Examiner* — Navin Natnithithadha
*Assistant Examiner* — Sunita Reddy
(74) *Attorney, Agent, or Firm* — Bose Corporation (57) ABSTRACT

An earphone includes a loudspeaker, a microphone, a housing supporting the loudspeaker and microphone, and an ear tip surrounding the housing and configured to acoustically couple both the loudspeaker and the microphone to an ear canal of a user, and to acoustically close the entrance to the user's ear canal. A processor receives input audio signals from the microphone, detects peaks having a frequency of around 1 Hz in the input audio signals, based on the detected peaks, computes an instantaneous heart rate, measures a frequency of an oscillation within the instantaneous heart rate, and based on the frequency of the oscillation, computes a rate of respiration.

21 Claims, 5 Drawing Sheets

(51) Int. Cl.
  *A61B 5/00* (2006.01)
  *H04R 3/00* (2006.01)
  *A61M 21/00* (2006.01)

(52) U.S. Cl.
  CPC ......... *H04R 1/1016* (2013.01); *H04R 1/1041* (2013.01); *H04R 1/1075* (2013.01); *H04R 3/005* (2013.01); *A61M 2021/0027* (2013.01); *A61M 2021/0061* (2013.01); *A61M 2021/0083* (2013.01); *A61M 2021/0088* (2013.01); *A61M 2205/3303* (2013.01); *A61M 2205/3375* (2013.01); *A61M 2205/42* (2013.01); *A61M 2205/50* (2013.01); *A61M 2205/8212* (2013.01); *A61M 2210/0662* (2013.01); *A61M 2230/06* (2013.01); *A61M 2230/42* (2013.01)

(58) Field of Classification Search
  CPC .. A61M 2021/0027; A61M 2210/0662; A61M 2205/3375; A61M 2205/42; A61M 2205/8212; A61M 21/02; A61M 2230/42; A61M 2230/06; A61M 2205/3303; H04R 3/005; H04R 1/1075; H04R 1/1041; H04R 1/1016; A61B 5/6803; A61B 5/6817
  USPC ................................ 600/26–28; 128/897–899
  See application file for complete search history.

(56) References Cited

U.S. PATENT DOCUMENTS

| | | | |
|---|---|---|---|
| 9,635,452 B2 | 4/2017 | Cheng et al. | |
| 2002/0091049 A1* | 7/2002 | Hisano | A63B 71/0686 482/148 |
| 2004/0077934 A1* | 4/2004 | Massad | A61B 5/0205 600/300 |
| 2007/0118011 A1* | 5/2007 | Harrison | H04R 25/456 600/25 |
| 2008/0146890 A1* | 6/2008 | LeBoeuf | A61B 5/0059 600/300 |
| 2008/0171945 A1* | 7/2008 | Dotter | A61B 5/024 600/514 |
| 2009/0143636 A1* | 6/2009 | Mullen | A61B 5/0476 600/26 |
| 2010/0125218 A1* | 5/2010 | Haartsen | A61B 5/02438 600/528 |
| 2010/0240945 A1* | 9/2010 | Bikko | A61B 5/02405 600/28 |
| 2011/0295083 A1* | 12/2011 | Doelling | A61B 5/103 600/301 |
| 2012/0203077 A1 | 8/2012 | He et al. | |
| 2012/0225412 A1* | 9/2012 | Wagner | A61B 5/0205 434/236 |
| 2012/0256933 A1 | 10/2012 | Airey et al. | |
| 2013/0034258 A1* | 2/2013 | Lin | A61F 11/08 381/380 |
| 2013/0090567 A1 | 4/2013 | Lee et al. | |
| 2014/0141395 A1* | 5/2014 | Gavish | A61B 5/0205 434/236 |
| 2015/0150515 A1 | 6/2015 | Strachan | |
| 2015/0154950 A1* | 6/2015 | Ring | H04R 1/1083 381/71.6 |
| 2015/0258301 A1 | 9/2015 | Trivedi et al. | |
| 2015/0351688 A1* | 12/2015 | Just | A61B 5/681 600/407 |
| 2016/0151603 A1* | 6/2016 | Shouldice | H04R 3/00 600/28 |
| 2017/0061760 A1 | 3/2017 | Lee et al. | |
| 2017/0094385 A1 | 3/2017 | Lee et al. | |
| 2017/0149945 A1 | 5/2017 | Lee et al. | |
| 2017/0325718 A1 | 11/2017 | Boesen et al. | |
| 2017/0347177 A1 | 11/2017 | Masaki et al. | |
| 2017/0367658 A1 | 12/2017 | LeBoeuf et al. | |
| 2018/0078197 A1 | 3/2018 | Ware et al. | |
| 2018/0078198 A1 | 3/2018 | Reich et al. | |
| 2018/0078732 A1 | 3/2018 | Keshavan et al. | |
| 2018/0078733 A1 | 3/2018 | Freed et al. | |
| 2018/0081527 A1 | 3/2018 | Dolecki et al. | |
| 2018/0082550 A1 | 3/2018 | Read et al. | |
| 2018/0338193 A1 | 11/2018 | Wallace et al. | |
| 2019/0022349 A1 | 1/2019 | Kirszenblat et al. | |
| 2019/0028789 A1 | 1/2019 | Stockton et al. | |

FOREIGN PATENT DOCUMENTS

| | | |
|---|---|---|
| WO | 2017011431 A2 | 1/2017 |
| WO | 2017068571 A1 | 4/2017 |
| WO | 2017203251 A1 | 11/2017 |

OTHER PUBLICATIONS

International Search Report and Written Opinion dated Oct. 10, 2018 for International application No. PCT/US2018/043061.
International Search Report and Written Opinion dated Oct. 10, 2018 for International application No. PCT/US2018/043062.
Axel Schafer et al: "Estimation of Breathing Rate from Respiratory Sinus Arrhythmia: Comparison of Various Methods", Annals of Biomedical Engnieering, Kluwer Academic Publishers-Plenum Publishers, NE, vol. 36, No. 3, Jan. 11, 2008 (Jan. 11, 2008), pp. 476-485, XP019568785, ISSN: 1573-9686, pp. 476-p. 480.
Richard Singhathip et al: "Extracting Respiration Rate From Raw ECG Signals", Biomedical Engineering: Applications, Basis and Communications = Yixue-Gongc, World Scientific, TW, vol. 22, No. 4, Aug. 1, 2010 (Aug. 1, 2010), pp. 307-314, XP008169483, ISSN : 1016-2372, DOI: 10.4015/S1016237210002079 pp. 307-p. 309.
Kim J M et al: "Two Algorithms for Detecting Respiratory Rate from ECG Signal", Imaging the Future Medicine : World Congress on Medical Physics and Biomedical Engineering 2006, Aug. 27-Sep. 1, 2006, Coex Seoul, K; [IFMBE Proceedings, vol. 14], Springer, DE, vol. 14, Jan. 1, 2007 (Jan. 1, 2007), pp. 4069-4071, XP008169469, DOI: 10 .1007/978-3-540-36841-0 1030 ISBN : 978-3-540-36839-7—the whole document.
International Search Report and Written Opinion dated Apr. 26, 2019 for PCT/US2019/014772.
International Search Report and Written Opinion dated Jul. 3, 2019 for PCT/US2019/014066.
Invitation to Pay Additional Fees and Partial International Search Report dated May 2, 2019 for PCT/US2019/014066.

\* cited by examiner

EARPHONES FOR MEASURING AND ENTRAINING RESPIRATION

RELATED APPLICATIONS

This application is related to, and incorporates by reference, U.S. patent application Ser. No. 15/106,989, filed Jun. 21, 2016; Application Ser. No. 15/348,400, filed Nov. 10, 2016; and application Ser. No. 15/352,034, filed Nov. 17, 2016, all titled Intelligent Earplug System. It is also related to U.S. patent application Ser. No. 15/267,567, entitled Sleep Assistance Device; application Ser. No. 15/267,464, entitled Sleep Quality Scoring and Improvement; application Ser. No. 15/267,552, entitled Intelligent Wake-Up System; application Ser. No. 15/267,848, entitled Sleep System; application Ser. No. 15/267,858, entitled User Interface for a Sleep System; and application Ser. No. 15/267,886, entitled Sleep Assessment Using a Home Sleep System, all of which were filed on Sep. 16, 2016. It is also related to U.S. patent application Ser. No. 15/655,836, titled Sleep Assistance Device For Multiple Users, filed Jul. 20, 2017, now U.S. Pat. No. 10,478,590, which is incorporated here by reference.

BACKGROUND

This disclosure relates to earphones for measuring and entraining respiration.

Sleeplessness and poor or interrupted sleep may significantly affect a person's health. Poor sleep may be caused by such factors as ambient noise, stress, medical conditions, or discomfort. Thus, there exists a need for a sleep aid that can help address the underlying causes of poor sleep without adversely affecting the user's health in other, unintended ways.

SUMMARY

In general, in one aspect, a system includes an earphone including a loudspeaker, a microphone, a housing supporting the loudspeaker and microphone, and an ear tip surrounding the housing and configured to acoustically couple both the loudspeaker and the microphone to an ear canal of a user, and to acoustically close the entrance to the user's ear canal. A processor receives input audio signals from the microphone, detects peaks having a frequency of around 1 Hz in the input audio signals, based on the detected peaks, computes an instantaneous heart rate, measures a frequency of an oscillation within the instantaneous heart rate, and based on the frequency of the oscillation, computes a rate of respiration.

Implementations may include one or more of the following, in any combination. The processor may measure the frequency of the oscillation within the instantaneous heart rate by computing a fast Fourier transform (FFT) of the instantaneous heart rate. The processor may measure the frequency of the oscillation within the instantaneous heart rate by computing a gradient of the instantaneous heart rate, and computing a fast Fourier transform (FFT) of the gradient of the instantaneous heart rate. The processor may measure the frequency of the oscillation within the instantaneous heart rate by detecting peaks of the instantaneous heart rate. The processor may measure the frequency of the oscillation within the instantaneous heart rate by fitting a sine function to the instantaneous heart rate, the frequency of the sine curve being the frequency of the oscillation.

The system may include a second earphone, which would include a second loudspeaker, a second microphone, a second housing supporting the second loudspeaker and second microphone, and a second ear tip surrounding the second housing and configured to acoustically couple both the second loudspeaker and the second microphone to a second ear canal of the user, and to acoustically close the entrance to the user's second ear canal, with the processor receiving second input audio signals from the microphone, and detecting the peaks having a frequency of around 1 Hz by combining the input audio signals from the first microphone with the second input audio signals, and detecting peaks within the result of the combination. Combining the input audio signals may include multiplying the amplitude of the first input audio signals by the amplitude of the second input audio signal, at each time that the two signals may be sampled. The processor may adjust output audio signals based on the rate of respiration, and provide the output audio signals to the loudspeaker. Adjusting the output audio signals may include adjusting a rhythm of the output audio signals to be about one cycle per minute less than the detected respiration rate. Adjusting the output audio signals may include transitioning the output audio signals from respiration entrainment sounds to masking sounds. Adjusting the output audio signals may include transitioning the output audio signals from masking sounds to awakening sounds. The earphone may include a memory storing sound files, and providing the output audio signals may include retrieving a first sound file from the memory. Adjusting the output audio signals may include retrieving a second sound file from the memory and using the second sound file to generate the output audio signal. The processor may be integrated within the earphone. The processor may be integrated within a portable computing device.

In general, in one aspect, measuring the respiration rate of a user of an earphone includes receiving input audio signals from a microphone supported by a housing and acoustically coupled to the user's ear canal by an ear tip surrounding the housing and acoustically closing the entrance to the user's ear canal, and in a processor, detecting peaks having a frequency of around 1 Hz in the input audio signals, based on the detected peaks, computing an instantaneous heart rate, measuring a frequency of an oscillation within the instantaneous heart rate, and based on the frequency of the oscillation, computing a rate of respiration.

Advantages include acoustically sensing the respiration rate at the ear without interference from audio signals being generated by the earphone.

All examples and features mentioned above can be combined in any technically possible way. Other features and advantages will be apparent from the description and the claims.

DESCRIPTION

Several of the above-referenced applications describe a bedside system that detects a user's respiration rate and uses that to infer and manage their sleep state. In particular, to assist the user with falling to sleep, the system plays sounds that have a rhythm slightly slower than the user's own respiration rate. This naturally leads the user to slow their breathing to match the rhythm of the sounds, in a process referred to as entrainment. As the user slows their rate of respiration, the rate of the sounds is further reduced, in a feedback loop that leads the user gradually to sleep. Once the user falls asleep (as indicated by artifacts in their respiration rate), the system switches to playing masking sounds, which diminish the user's ability to detect, and be disturbed by, external sounds. If the user is detected to be waking up too early, entrainment may be reactivated. When it is time for the user to wake up, the system may coordinate wake-up sounds with the user's sleep state and other information to wake the user in the least-disruptive way possible.

Others of the above-referenced applications describe intelligent earplugs which the user can wear while sleeping, and which provide masking sounds through the night, and alarm or alert sounds when needed. These earplugs are controlled by a smartphone, but principally operate autonomously, playing stored masking sounds until instructed otherwise by the controlling phone, or based on an internal clock. It would be advantageous if the intelligent earplugs could play the respiration-entraining sounds of the bedside systems, to help the user fall asleep without disturbing others who may be sharing the bed or room. One solution to that, described in U.S. patent application Ser. No. 15/655,836, is for the sleep system to inform the earplugs of the user's respiration rate and sleep state, and for the earplugs to adjust the rate of a rhythmic component in stored entrainment sounds as in the out-loud system.

This disclosure describes how to add respiration sensing to the earplugs themselves, so that the external system is not required, and the earplugs can operate fully autonomously, or with only a smart phone to control them.

Figure 1:
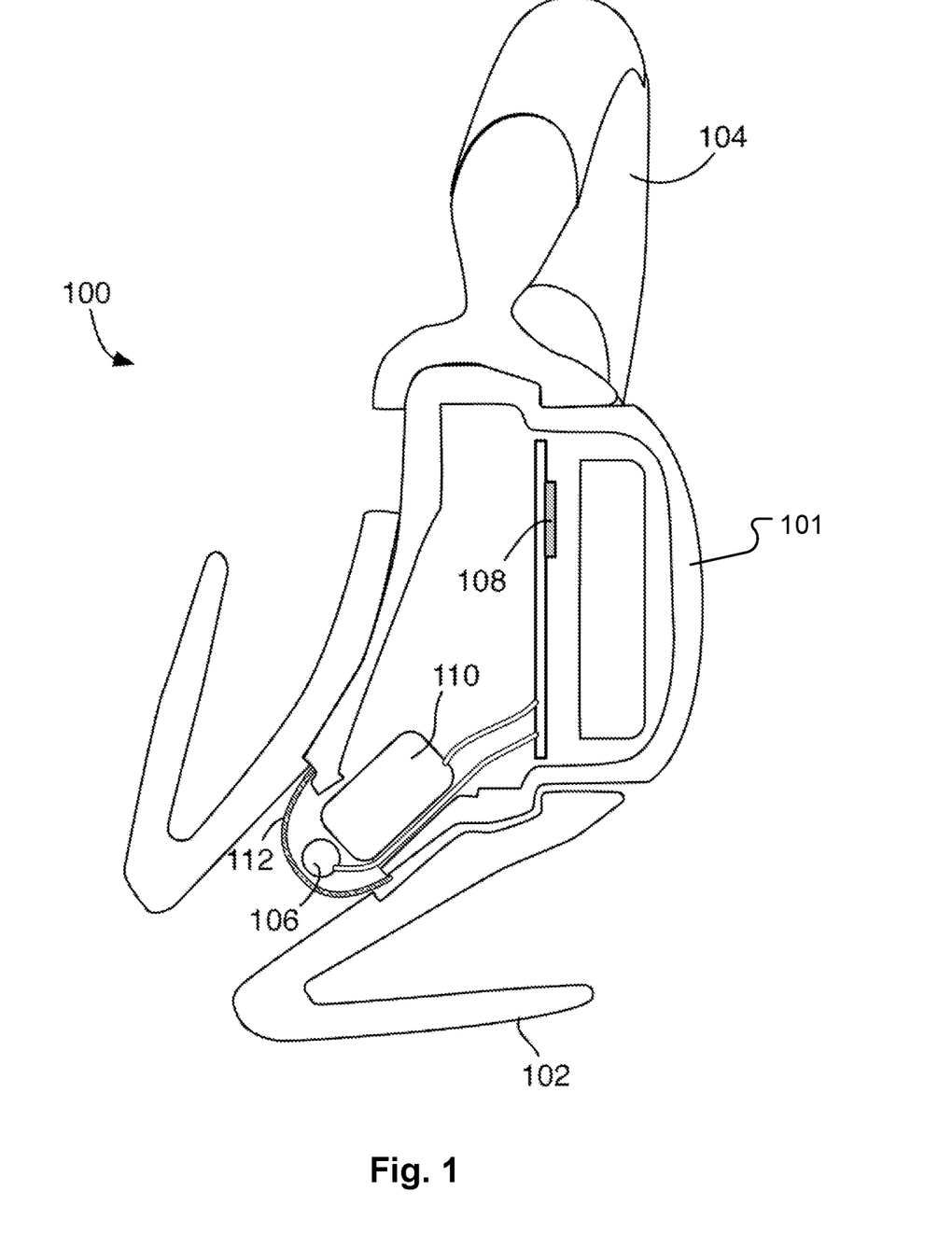
FIGS. 1 and 2 show cross-sectional views of earphones with an integrated microphones.
Figure 2:
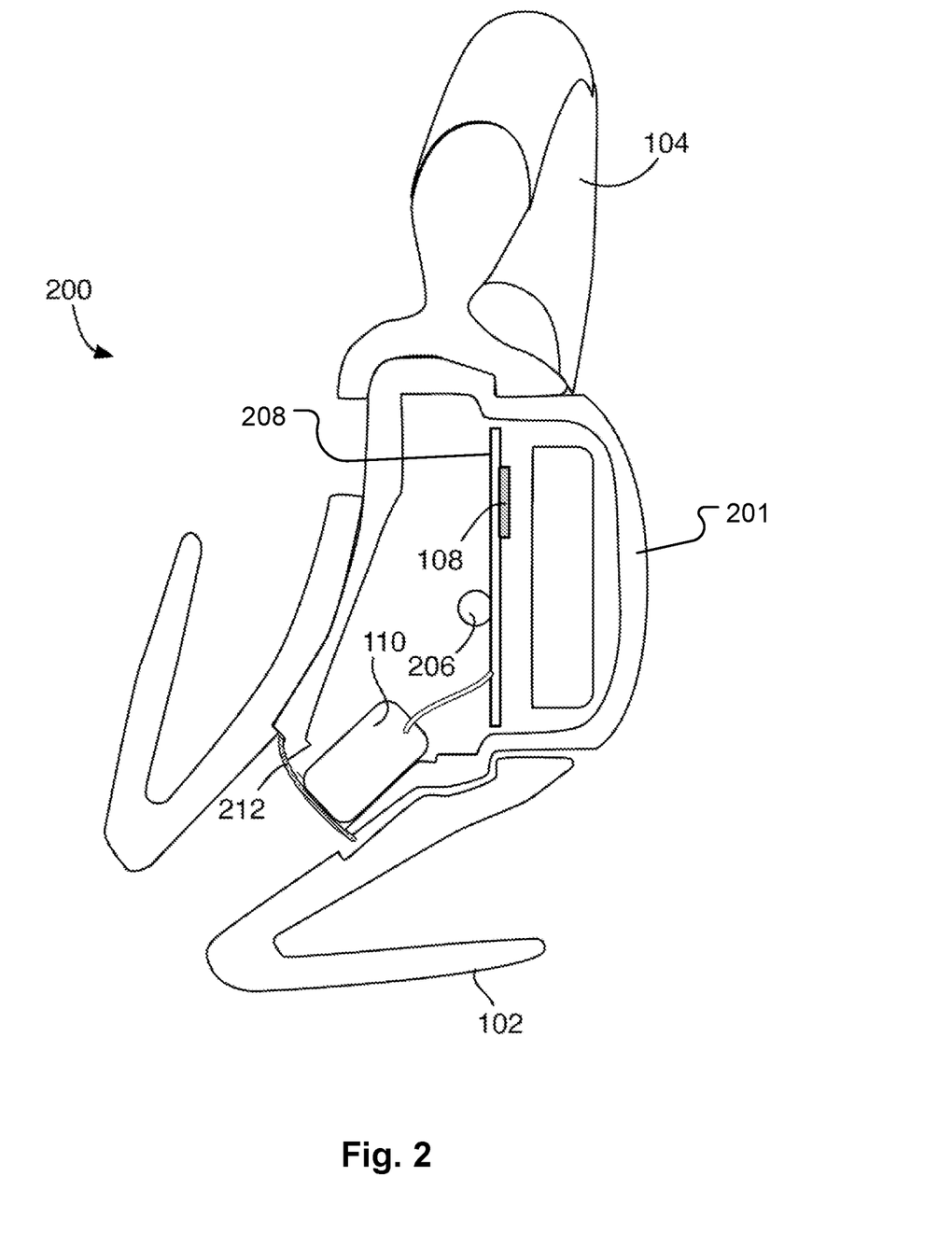
Figure 3:
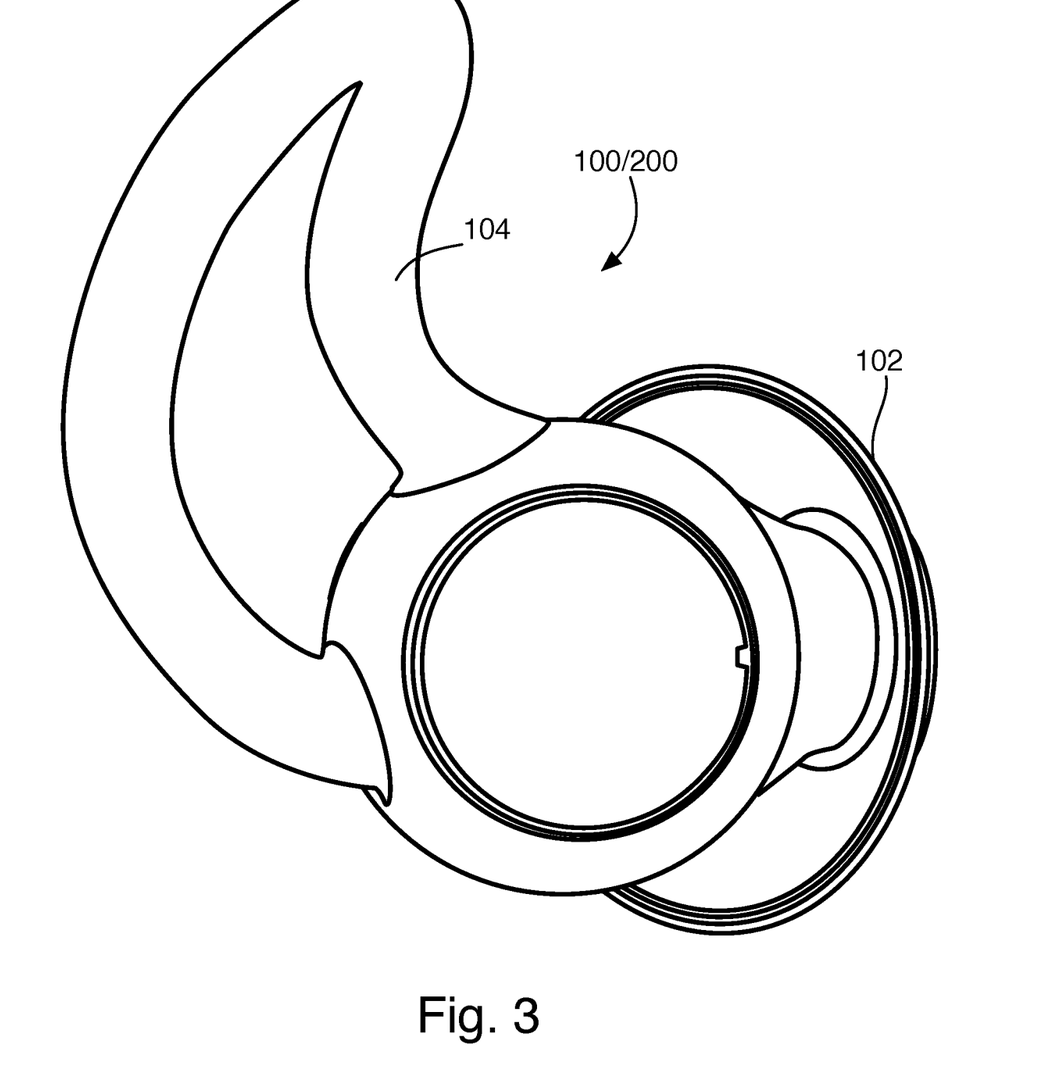
FIG. 3 shows an external view of the system of FIG. 1 or 2.

As shown in FIGS. 1, 2 and 3, sleep-sensing earphones 100 or 200 include an ear tip sealing structure 102 that blocks, or occludes, the entrance to the ear canal. FIGS. 1 and 2 show cross-sections of two different earphone examples, while FIG. 3 shows an exterior view, which is the same for the examples of either FIG. 1 or 2, for reference. A retaining structure 104 helps retain the earphone in the ear, and puts pressure on the sealing structure 102 to maintain the seal by pushing on the concha, opposite to where the sealing structure meets the ear canal. The sealing structure 102 helps to passively block outside sounds from entering the ear, increasing the effectiveness of the masking sounds played by the earphones.

Another result of occluding the ear canal is that sounds produced by the body, such as the heartbeat and respiration sounds, are amplified within the ear canal. With the addition of a microphone 106 (FIG. 1) or 206 (FIG. 2), the heartbeat can be sensed and its rate determined. The processor 108 on-board each earphone (or in one, if they coordinate their action) can then extract the respiration rate from the heartbeat signal, and adjust the timing of entrainment sounds being played to the user through a speaker 110. In the example of FIG. 1, the microphone 106 and speaker 110 are shown behind a screen 112, as described in U.S. Pat. No. 9,635,452, which is incorporated here by reference. The microphone may be mounted near or on the speaker 110, or integrated into the speaker housing. In the example of FIG. 2, the microphone 206 is mounted directly to the PCB 208 and the screen 212 is flat, or may not be needed; the volume inside the earbud is coupled to the ear canal via space around the speaker 110. As long as the earbud/ear canal system is effectively sealed at the frequencies of interest, the microphone will detect the targeted sounds coming from inside the ear canal. A housing 101 (FIG. 1) or 201 (FIG. 2) supports the speaker 110 and the microphone 106 (FIG. 1) or 206 (FIG. 2).

Figure 4:
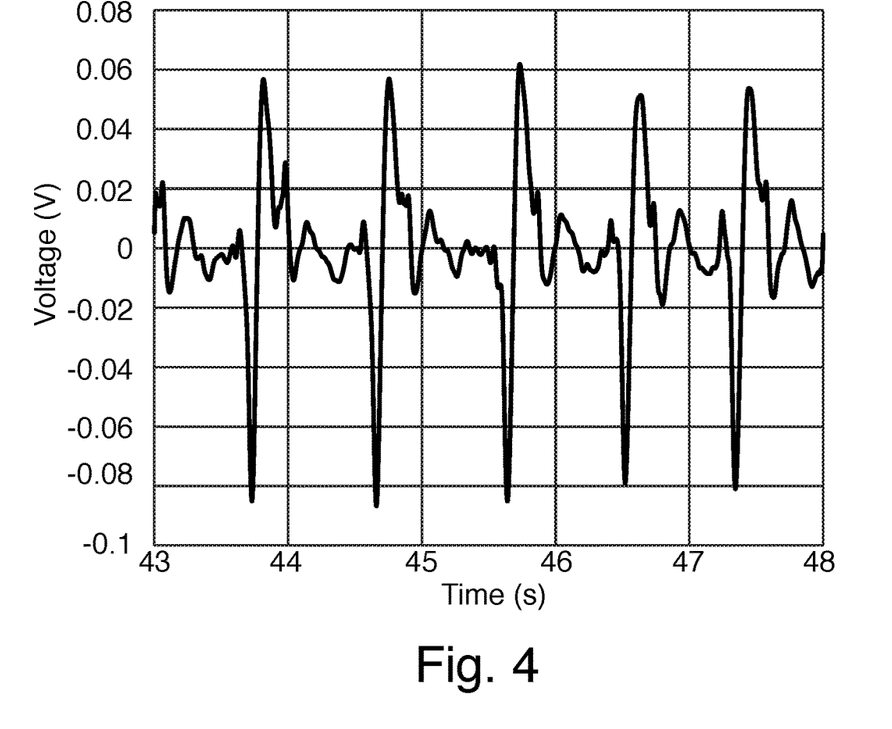
FIGS. 4-6 show graphs of sensor readings
Figure 5:
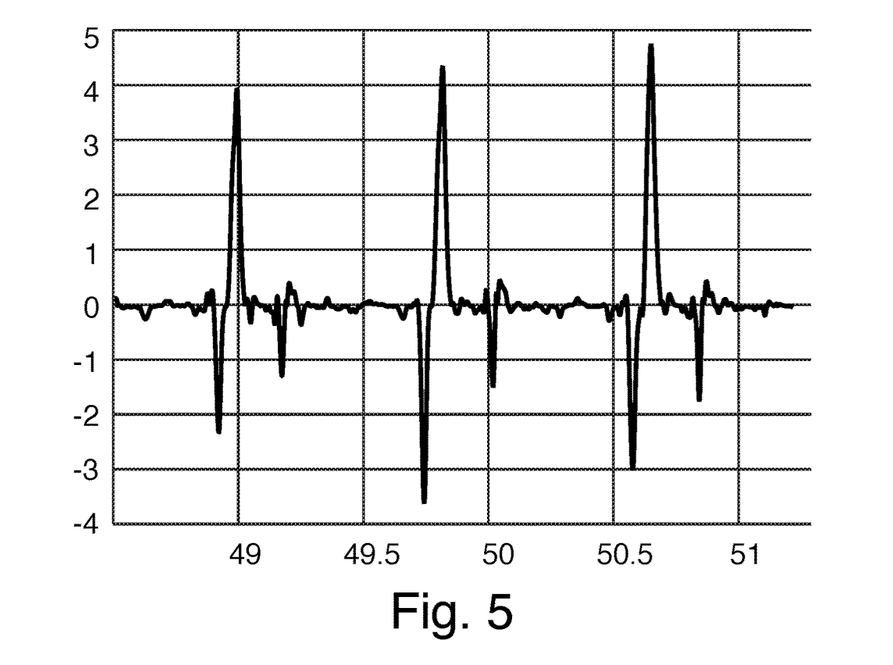

The heartbeat is derived from the microphone signals, and the respiration rate is derived from the heart rate variability. Specifically, as shown in FIG. 4, the microphone coupled to the occluded ear canal detects heartbeats as energy peaks in a signal with a frequency of around 8-10 Hz (the heart rate itself is around 1 Hz). As this rate is far below the frequency range of the masking sounds, those sounds will not interfere with detecting the heartbeat. If both ears are equipped with microphones, and the signals are transmitted to the smart phone (or from one ear to the other) for analysis, combining the amplitudes of the two signals at each time sample, such as by multiplication, can greatly increase the signal to noise ratio, as shown in FIG. 5. Applying a peak-finding algorithm to the microphone signal and observing the distance between consecutive peaks yields the beat-to-beat, or instantaneous, heart rate value, shown in FIG. 6.

Figure 6:
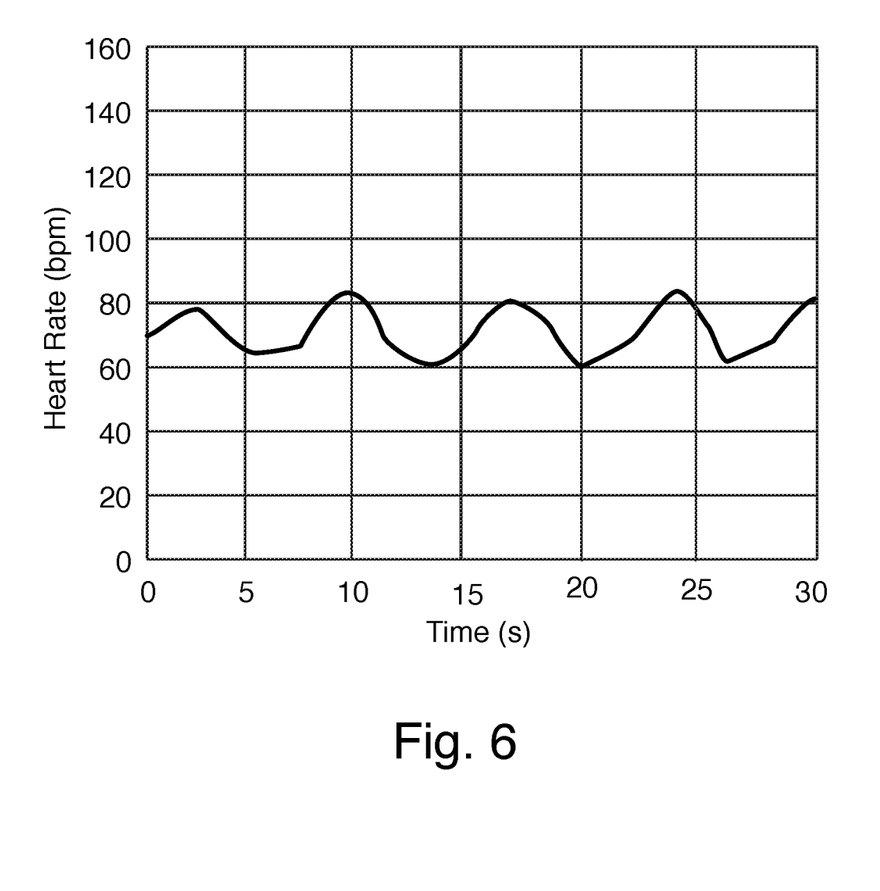

FIG. 6 shows that there is a cyclic variability to the instantaneous heart rate. The period of this variability happens to be the respiration rate—as the user inhales, their heart rate increases, and as they exhale, their heart rate decreases. Applying another peak detection step, or other frequency analysis such as a fast Fourier transform (FFT) or fitting a sine function to the curve, to the instantaneous heart rate or to its gradient, reveals the respiration rate.

If the earphones happen to include a feedback-based active noise reduction (ANR) system, to further block environmental sounds, the system microphone of the ANR system would be more than adequate for detecting the sound of blood flow and measuring the heart rate. However, an ANR system is likely to consume a lot of power, and may not be suitable or necessary for sleep-focused earphones. Since the respiration and heart rate sensing is very narrow-band, a simpler MEMS microphone should be sufficient, and a much lower-power component may be used, benefiting the overall battery life and component size of the earphones. Similarly, it may be possible to use an external device, such as a smartphone, to filter and demodulate the microphone signals to detect the heart rate and extract the respiration rate from it, and to modify the output sounds accordingly, but battery life may be better served by doing all the processing within the earphones. The trade-off between power for processing and power for communication may depend on factors unrelated to the acoustics, including battery size, antenna placement, and memory requirements, to name a few.

Embodiments of the systems and methods described above comprise computer components and computer-implemented steps that will be apparent to those skilled in the art. For example, it should be understood by one of skill in the art that the computer-implemented steps may be stored as computer-executable instructions on a computer-readable medium such as, for example, hard disks, optical disks, solid-state disks, flash ROMS, nonvolatile ROM, and RAM. Furthermore, it should be understood by one of skill in the art that the computer-executable instructions may be executed on a variety of processors such as, for example, microprocessors, digital signal processors, and gate arrays. For ease of exposition, not every step or element of the systems and methods described above is described herein as part of a computer system, but those skilled in the art will recognize that each step or element may have a corresponding computer system or software component. Such computer system and software components are therefore enabled by describing their corresponding steps or elements (that is, their functionality), and are within the scope of the disclosure.

A number of implementations have been described. Nevertheless, it will be understood that additional modifications may be made without departing from the scope of the inventive concepts described herein, and, accordingly, other embodiments are within the scope of the following claims.

What is claimed is:

1. A system comprising:
an earphone comprising:
  a loudspeaker;
  a microphone;
  a housing supporting the loudspeaker and the microphone; and
  an ear tip surrounding the housing, the ear tip being configured to acoustically couple both the loudspeaker and the microphone to an ear canal of a user, and to acoustically close the entrance to the user's ear canal;
a second earphone comprising:
  a second loudspeaker;
  a second microphone;
  a second housing supporting the second loudspeaker and the second microphone; and
  a second ear tip surrounding the second housing, the second ear tip being configured to acoustically couple both the second loudspeaker and the second microphone to a second ear canal of the user, and to acoustically close the entrance to the user's second ear canal; and
a processor configured to:
  receive input audio signals from the microphone;
  receive second input audio signals from the second microphone;
  detect peaks having a frequency of around 1 Hz in the input audio signals by combining the input audio signals from the first microphone with the second input audio signals, and detecting peaks within the result of the combination;
  based on the detected peaks, compute an instantaneous heart rate;
  measure a frequency of an oscillation within the instantaneous heart rate; and
  based on the frequency of the oscillation, compute a rate of respiration.

2. The system of claim 1, wherein the processor is configured to measure the frequency of the oscillation within the instantaneous heart rate by computing a fast Fourier transform (FFT) of the instantaneous heart rate.

3. The system of claim 1, wherein the processor is configured to measure the frequency of the oscillation within the instantaneous heart rate by
  computing a gradient of the instantaneous heart rate; and
  computing a fast Fourier transform (FFT) of the gradient of the instantaneous heart rate.

4. The system of claim 1, wherein the processor is configured to measure the frequency of the oscillation within the instantaneous heart rate by detecting peaks of the instantaneous heart rate.

5. The system of claim 1, wherein the processor is configured to measure the frequency of the oscillation within the instantaneous heart rate by fitting a sine function to the instantaneous heart rate, the frequency of the sine curve being the frequency of the oscillation.

6. The system of claim 1, wherein combining the input audio signals comprises multiplying the amplitudes of the first and second input audio signals, at each time that the two signals are sampled.

7. The system of claim 1, wherein the processor is further configured to adjust output audio signals based on the rate of respiration, and provide the output audio signals to the loudspeaker.

8. The system of claim 7, wherein adjusting the output audio signals comprises adjusting a rhythm of the output audio signals to be about one cycle per minute less than the detected respiration rate.

9. The system of claim 7, wherein adjusting the output audio signals comprises transitioning the output audio signals from respiration entrainment sounds to masking sounds.

10. The system of claim 7, wherein adjusting the output audio signals comprises transitioning the output audio signals from masking sounds to awakening sounds.

11. The system of claim 7, wherein
  the earphone further includes a memory storing sound files; and
  providing the output audio signals comprises retrieving a first sound file from the memory.

12. The system of claim 11, wherein adjusting the output audio signals comprises retrieving a second sound file from the memory and using the second sound file to generate the output audio signals.

13. The system of claim 1, wherein the processor is integrated within the earphone.

14. The system of claim 1, wherein the processor is integrated within a portable computing device.

15. A method of measuring a respiration rate of a user of an earphone, the method comprising:
  receiving input audio signals from a microphone supported by a housing and acoustically coupled to the user's ear canal by an ear tip surrounding the housing, the ear tip acoustically closing the entrance to the user's ear canal;
  receiving second input audio signals from a second microphone supported by a second housing and acoustically coupled to the user's second ear canal by a second ear tip surrounding the second housing, the second ear tip acoustically closing the entrance to the user's second ear canal; and
  in a processor,
  detecting peaks having a frequency of around 1 Hz in the input audio signals by combining the input audio signals from the first microphone with the second input audio signals, and detecting peaks within the result of the combination,
  based on the detected peaks, computing an instantaneous heart rate,
  measuring a frequency of an oscillation within the instantaneous heart rate, and
  based on the frequency of the oscillation, computing a rate of respiration.

16. The method of claim 15, wherein measuring the frequency of the oscillation within the instantaneous heart rate comprises computing a fast Fourier transform (FFT) of the instantaneous heart rate.

17. The method of claim 15, wherein measuring the frequency of the oscillation within the instantaneous heart rate comprises:
  computing a gradient of the instantaneous heart rate; and
  computing a fast Fourier transform (FFT) of the gradient of the instantaneous heart rate.

18. The method of claim 15, wherein measuring the frequency of the oscillation within the instantaneous heart rate comprises detecting peaks of the instantaneous heart rate.

19. The method of claim 15, wherein measuring the frequency of the oscillation within the instantaneous heart rate comprises fitting a sine function to the instantaneous heart rate, the frequency of the sine curve being the frequency of the oscillation.

20. The method of claim 15, wherein combining the input audio signals comprises multiplying the amplitudes of the first and second input audio signals, at each time that the two signals are sampled.

21. The method of claim 15, further comprising, in the processor:

adjusting output audio signals based on the rate of respiration, and providing the output audio signals to the loudspeaker.

\* \* \* \* \*